United States Patent [19]

Meixner et al.

[11] Patent Number: 4,870,152
[45] Date of Patent: Sep. 26, 1989

[54] PROCESS FOR THE PRODUCTION OF COMPOUNDS CONTAINING ISOCYANURATE GROUPS AND OLEFINIC DOUBLE BONDS AND THEIR USE AS BINDERS

[75] Inventors: Jürgen Meixner, Krefeld, Fed. Rep. of Germany; Manfred Bock, Pittsburgh, Pa.; Josef Pedain, Cologne, Fed. Rep. of Germany; Manfred Schönfelder, Leverkusen, Fed. Rep. of Germany

[73] Assignee: Bayer Aktiengesellschaft, Leverkusen, Fed. Rep. of Germany

[21] Appl. No.: 262,623

[22] Filed: Oct. 26, 1988

[30] Foreign Application Priority Data

Nov. 3, 1987 [DE] Fed. Rep. of Germany ....... 3737244

[51] Int. Cl.$^4$ ............................................. C08G 18/67
[52] U.S. Cl. ...................................................... 528/49
[58] Field of Search ........................................ 528/49

[56] References Cited

U.S. PATENT DOCUMENTS 4,246,391 1/1981 Watson ................................. 528/49

Primary Examiner—Maurice J. Welsh
Attorney, Agent, or Firm—Connolly and Hutz

[57] ABSTRACT

Binders which are hardenable by radiation or peroxides and are useful in coating compositions are compounds containing isocyanurate groups and olefinic double bonds produced by the reaction of components (a), (b) and (c) wherein (a) is a polyisocyanate component containing isocyanurate polyisocyanates which is
  (i) N,N′,N″-tris-(isocyanatohexyl)-isocyanurate alone or in admixture with its higher homologs containing more than one isocyanurate ring or
  (ii) mixtures of the polyisocyanates (i) with up to 40 NCO-equivalent-%, based on the total component (a), of other polyisocyanates containing aliphatically or cycloaliphatically bound isocyanate groups;

(b) is an olefinically unsaturated alcohol component comprising at least one hydroxyalkyl ester of acrylic acid or methacrylic acid; and (c) is a polyol component consisting essentially of a polyester polyol having an OH value of 80 to 350 based on (i) an acid component, of which at least 80 carboxyl equivalent-% is adipic acid, isophthalic acid or a mixture of both and (ii) a polyhydroxy component of which at least 70 hydroxyl equivalent-% is hexane-1, 6-diol;

wherein component (c) amounts to 20 to 150% by weight, based on the weight of component (b), and the reaction is carried out at with an NCO:OH equivalent ratio maintained at 0.9:1 to 1.1:1, and wherein components (b) and (c) are reacted with the polyisocyanate component in any order or in admixture.

6 Claims, No Drawings

PROCESS FOR THE PRODUCTION OF COMPOUNDS CONTAINING ISOCYANURATE GROUPS AND OLEFINIC DOUBLE BONDS AND THEIR USE AS BINDERS

This invention relates to a new process for the production of compounds containing isocyanurate groups and olefinic double bonds which are suitable for the production of coatings showing improved lacquer properties and to the use of the new compounds as binders.

BACKGROUND OF THE INVENTION

Urethane (meth)acrylates, their production by reaction of organic polyisocyanates with hydroxyalkyl (meth)acrylates and their use as binders for coating compositions hardenable by UV radiation or by electron beams are known, for example, from German 1,644,779; German 2,115,373; German 2,734,237; German 3,118,147; and British 1,491,695.

The object of the present invention is to provide urethane (meth)acrylates which may even be hardened with peroxides in the absence of air and which, at the same time, are at least equivalent to the systems of the above-mentioned prior art in regard to the lacquer properties of the resulting coatings.

This object of the invention is achieved by the binder compounds containing isocyanurate groups and olefinic double bonds prepared by the process according to the invention described hereinafter.

BRIEF DESCRIPTION OF THE INVENTION

Binder compounds containing isocyanurate groups and olefinic double bonds which are hardenable by radiation or peroxides are prepared by reacting (a) a polyisocyanate component containing at least N,N',N"-tris-(isocyanatohexyl)-isocyanurate, (b) hydroxyalkyl ester of acrylic or methacrylic acid, and (c) a polyester polyol.

DETAILED DESCRIPTION

The present invention relates to a process for the production of compounds containing isocyanurate groups and olefinic double bonds by reaction of
(a) a polyisocyanate component containing isocyanurate polyisocyanates with
(b) an olefinically unsaturated alcohol component consisting of at least one hydroxyalkyl ester of acrylic acid or methacrylic acid, characterized in that
  (a) the polyisocyanate component is (i) N,N',N"-tris-(isocyanatohexyl)-isocyanurate optionally present in admixture with its higher homologs containing more than one isocyanurate ring or (ii) mixtures of the polyisocyanates mentioned under (i) with up to 40 NCO-equivalent-%, based on the total component (a), of other polyisocyanates containing aliphatically and/or cycloaliphatically bound isocyanate groups
and the reaction is carried out using
(c) a polyol component consisting essentially of a polyester polyol having an OH value of 80 to 350 based on (i) an acid component, of which at least 80 carboxyl equivalent-% consists of adipic acid and/or isophthalic acid and (ii) a polyol component of which at least 70 hydroxyl equivalent-% consists of hexane-1,6-diol, component (c) making up 20 to 150% by weight, based on the weight of component (b), and the reaction being carried out at an NCO:OH equivalent ratio maintained at 0.9:1 to 1.1:1, the alcoholic components (b) and (c) being reacted with the polyisocyanate component in any order or in admixture.

The present invention also relates to the compounds containing isocyanurate groups and olefinic double bonds obtained by this process as binders for coating compositions hardening under the effect of radiation or peroxides in the presence of air.

At leat 60 NCO equivalents-% of the polyisocyanate component (a) to be used in the process according to the invention consists of N,N',N"-tris-(6-isocyanatohexyl)-isocyanurate or of mixtures thereof with its higher homologs containing more than one isocyanurate ring. The production of such trimers of 1,6-diisocyanatohexane is described, for example, in EP-A-10 589 or U.S. Pat. No. 4,324,879. Up to 50% by weight, based on the mixture, of higher homologs of the type mentioned are generally present in the mixtures mentioned. The polyisocyanate component (a) may contain up to 40 NCO equivalent-% of other polyisocyanates containing aliphatically and/or cycloaliphatically bound isocyanate groups. These other polyisocyanates are, for example, 1,6-diisocyanatohexane, 1-isocyanato-3,3,5-trimethyl-5-isocyanatomethyl cyclohexane (IPDI), isocyanurate polyisocyanates based on IPDI or urethane polyisocyanates based on IPDI and polyhydric alcohols, such as for example trimethylolpropane. At least 95 NCO equivalent-% of the polyisocyanate component (a) preferably consists of N,N',N"-tris-(6-isocyanatohexyl)-isocyanurate or the above-mentioned mixtures thereof with its higher homologs.

The alcohol component (b) is at least one hydroxyalkyl ester of acrylic acid or methacrylic acid, i.e. simple esters of these acids with dihydric aliphatic alcohols having a molecular weight in the range from 62 to 300. Suitable alcohols such as these are ethylene glycol, propane-1,2-diol, propane-1,3-diol, the isomeric butanediols, pentanediols or hexanediols, or, for example, diols containing ester groups based on these simple alkane diols and dibasic acids, such as for example adipic acid, providing the esters are within the molecular weight range mentioned. Component (b) is preferably 2-hydroxyethyl acrylate, 2-hydroxyethyl methacrylate, 2-hydroxypropyl acrylate, 2-hydroxypropyl methacrylate or mixtures of these compounds.

Component (c) is a polyester polyol having an OH value in the range from 80 to 350 which has been prepared in known manner by reaction of (i) 33 to 46 mol-% of a dicarboxylic acid component with (ii) 54 to 67 mol-% of a polyol component.

At least 80 carboxyl equivalent-% of the dicarboxylic acid component consists of adipic acid and/or isophthalic acid, preferably 0 to 80 mol-% of isophthalic acid and 20 to 100 mol-% of adipic acid. In addition to these two acids, small quantities of other dicarboxylic acids or dicarboxylic acid derivatives may also be used, including for example terephthalic acid, phthalic acid, phthalic anhydride, tetrahydrophthalic acid, tetrahydrophthalic anhydride, hexahydrophthalic acid and/or hexahydrophthalic anhydride. The carboxyl equivalent percentages shown above are based on the total quantity of dicarboxylic acids or dicarboxylic acid derivatives used for the preparation of component (c), the anhydrides mentioned by way of example entering into the calculation as "dicarboxylic acid".

The polyol component (ii) consists of the usual polyhydric alcohols, for example those mentioned by way of example above in connection with component (b); component (ii) may also contain higher alcohols, such as glycerol or trimethylolpropane, with the proviso that at least 70 hydroxyl equivalent-% of component (ii) for the preparation of component (c) consists of hexane-1,6-diol.

A polyester diol of hexane-1,6-diol and adipic acid is preferably used as component (c).

The acid values of component (c) are generally in the range from 1.0 to 10 while the molecular weight as calculated from the stoichiometry of the starting materials used is in the range from 250 to 3,000.

Component (c) is generally used in a quantity of 20 to 150% by weight and preferably in a quantity of 20 to 100% by weight, based on the weight of component (b).

To carry out the process according to the invention, components (b) and (c) are reacted in any order or in the form of a mixture of the two individual components with the polyisocyanate component (a) prepared beforehand, the NCO/OH equivalent ratio being kept at 0.9:1 to 1.1:1 and preferably at approximately 1:1. The reaction is generally carried out at a temperature in the range from 40° to 100° C. and preferably at a temperature in the range from 50° to 80° C., although it is important to ensure that there are no unwanted, heat-induced polymerization reactions. Accordingly, it is often best to carry out the reaction at relatively low temperatures within the ranges shown using known catalysts which accelerate the isocyanate addition reaction. Suitable catalysts are, for example, alkali metal alcoholates, such as sodium ethylate, tertiary amines, such as triethylamine, diethylenetriamine or dimethyl benzylamine, or for example known tin catalysts, such as tin dioctoate or dibutyltin dilaurate.

The reaction may be carried out in the absence or presence of inert solvents, such as for example ethyl acetate, butyl acetate, ethyl glycol acetate and/or methyl isobutyl ketone.

In order to protect the urethane acrylates according to the invention against unwanted premature polymerization, it is often advisable to add during their actual preparation from 0.001 to 0.3% by weight, based on the weight of the starting materials, of known polymerization inhibitors or antioxidants, such as for example the quinones, hydroquinones, copper compounds, phosphites, amines or phenols normally used for this purpose.

The products according to the invention are generally clear, medium- to high-viscosity, colorless liquids.

If their viscosity is too high for the desired application, they may be diluted with solvents. Solvents suitable for this purpose are aromatic hydrocarbons, such as for example toluene, xylene and more highly substituted benzenes, esters, such as for example ethyl acetate, butyl acetate, methoxy or ethoxy ethyl acetate, butoxyethyl acetate, and ketones, such as acetone, methyl ethyl ketone, methyl isobutyl ketone or cyclohexane, and also alcohols, such as methanol, ethanol, propanol, i-propanol, butanol, i-butanol, etc.

Ethylenically unsaturated low molecular weight compounds, such as for example esters of acrylic or methacrylic acid, aromatic vinyl compounds or vinyl alkyl ethers, may also be regarded as solvents in the broader sense.

These ethylenically unsaturated "solvents" in reality are not genuine solvents, but may instead be regarded as "reactive diluents" because they react off with the products according to the invention by copolymerization during the crosslinking reaction.

The products according to the invention are valuable binders for coatings. They may be used as such or in combination with the auxiliaries and additives known from lacquer technology, including for example fillers, pigments, solvents, levelling aids and the like, for the production of coatings on any substrates. Suitable substrates are paper, cardboard, leather, wood, plastics, nonwovens, textiles, ceramic materials, mineral materials, glass, metals, artificial leather, photographic materials such as, for example, paper coated with a photographic layer.

The coating compositions may be applied in known manner by spray coating, knife coating, roll coating, spread coating, dip coating or casting. After evaporation of any inert solvents used, the coatings may be crosslinked either by high-energy radiation, such as UV light, electrons or gamma rays, or by hardening with metal salts of siccative acids and (hydro)peroxides at temperatures between room temperature and 150° C.

Where crosslinking is initiated by UV irradiation, photoinitiators have to be added to the coating composition.

Suitable photoinitiators are the compounds normally used which are described, for example, in the book by J. Korsar entitled "Light-Sensitive Systems", J. Wiley & Sons, New York-London-Sydney 1965.

Other suitable photoinitiators are benzoin ethers, such as benzoin isopropyl ether, benzilketals, such as for example benzildimethylketal, and hydroxyalkyl phenones, such as for example 2-hydroxy-2-methyl-1-phenolpropan-1-one.

The photoinitiators mentioned, which are used in quantities of from 0.1 to 5% by weight, based on polymerizable components, depending on the purpose for which the compositions according to the invention are to be used, may be used either individually or, by virtue of frequent favorable synergistic effects, even in combination with one another.

The metal salts of siccative acids used where the urethane acrylates according to the invention are crosslinked with peroxides are, for example, cobalt, lead and manganese salts of such acids as linseed oil fatty acids, tall oil fatty acid, soya oil fatty acids, of resinic acids, such as abietic acid and naphthenic acid, or of acetic acid and isooctanoic acid. They are used in the form of organic solutions in such quantities that the metal content, based on urethane acrylate, corresponds to 0.005 to 1% by weight.

Examples of (hydro)peroxides are di-tert.-butyl peroxide, benzoyl peroxide, cyclohexanone peroxide, methyl ethyl ketone peroxide, acetyl acetone peroxide, dinonyl peroxide, bis-(4-tert.-butylcyclohexyl)-peroxydicarbonate, tert.-butyl hydroperoxide, cumene hydroperoxide, 2,5-dimethylhexane-2,5-hydroperoxide and diisopropylbenzene monohydroperoxide. These (hydro)peroxides are preferably used in quantities of 1 to 10% by weight, based on urethane acrylate.

In the following Examples, all percentages are percentages by weight.

EXAMPLES

The following starting materials are used in the following Examples:

Polyisocyanate I (Trimerized 1,6-diisocyanatohexane (HDI))

1 ml 2-dimethylaminomethyl nonylphenol is added at 23° C. to 1344 g HDI. After stirring for 5 minutes, 40 ml of a 2% solution of 2-hydroxyethyl trimethyl ammonium hydroxide in dimethylformamide/methanol (8:1) are added dropwise over a period of 15 minutes, again at 23° C.

During the dropwise addition, the temperature rises to 35° C. and, after another 45 minutes, to 40° C. The trimerization reaction is maintained at that temperature. After 6 hours, an NCO content of 40.5% is reached. The reaction product is stabilized with 0.3 ml nonafluorobutane sulfonic acid in 1 ml dimethylformamide, followed by thin-layer distillation in a high vacuum.

Yield: 417 g (31%).
Iodine color value (DIN 6162): 3.
NCO content: 22.0%.
Viscosity (25° C.): 3100 mPa.s.
Monomeric HDI: 0.18%.

Polyisocyanate II (Isocyanurate polyisocyanate based on 3-isocyanatomethyl-3,5,5-trimethyl-5-isocyanatocyclohexane (IPDI))

1332 g IPDI are heated to 80° C. 15 ml of a 6% solution of 2-hydroxyethyl trimethyl ammonium hydroxide in dimethylformamide/methanol (4:1) are slowly added dropwise uniformly over a period of 45 minutes, the temperature rising to around 88° C. (the temperature should not exceed 90° C.; if the temperature is too high, the trimerization reaction is non-specific and leads to relatively high viscosities of the end product). After the dropwise addition, the reaction mixture is stirred for 30 minutes, the temperature falling to 80° C. Thereafter, the NCO content of the trimer solution is 30.6%. After thin-layer distillation in a high vacuum, the resin is dissolved in ethyl glycol acetate to form a 75% solution.

Yield (resin): 580 g (44%).
Viscosity (solution): 5107 mPa.s (25° C.).
NCO content (solution): 12.5%.
Free IPDI (solution): 0.18%.

Polyester polyols I to III

The starting materials shown in Table 1 are mixed and heated in stages to 210° C. in an inert gas atmosphere. The esterification reaction is continued at that temperature with removal of the water of reaction by distillation until an acid value below 5 mg KOH/g is reached.

Colorless to pale yellowish soft resins forming clear solutions in standard solvents are obtained.

TABLE 1

|  | Polyester polyol | | |
|---|---|---|---|
|  | I | II | III |
| Quantity weighed in (%): | | | |
| Adipic acid | 13.2 | 10.2 | 42.2 |
| Phthalic anhydride | 6.6 | 5.0 | |
| Isophthalic acid | 37.6 | 28.9 | |
| Hexane-1,6-diol | 42.7 | 65.3 | 68.2 |
| Trimethylolpropane | 12.2 | | |
| Characteristic data: | | | |
| Acid value (mg KOH/g) | 2 | 4 | 2 |
| OH value (mg KOH/g) | 140 | 250 | 330 |

EXAMPLES 1 TO 3 (process according to the invention) and 4 TO 6 (Comparison Examples)

In all the Examples, the reaction is carried out in the presence of 0.05% hydroquinone and 0.025 dibutyltin dilaurate while air is passed through. The viscosity data are based on measurements in a rheometer at 23° C.

The polyisocyanates shown in Table 2 are dissolved in butyl acetate and heated to 60° C. Hydroxyethyl acrylate is then aded dropwise at such a rate that the temperature does not exceed 70° C. The particular polyester polyols are then added and the mixture kept at 60° C. until the NCo content has fallen to 0. The butyl acetate is used in such a quantity that the solids contents shown in Table 2 below, based on the total quantity weighed in, are obtained.

TABLE 2

|  | Examples | | | Comparison Examples | | |
|---|---|---|---|---|---|---|
|  | 1 | 2 | 3 | 4 | 5 | 6 |
| Quantity weighed in (%): | | | | | | |
| Polyisocyanate I | 59.8 | 66.7 | 66.4 | 67.6 | 64.4 | |
| Polyisocyanate II | | | | | | 72.1 |
| Hydroxyethyl acrylate | 30.2 | 24.5 | 22.6 | 27.4 | 35.6 | 21.0 |
| Hexane-1,6-diol | | | | 5.0 | | |
| Polyester polyol I | 10.0 | | | | | 6.9 |
| Polyester polyol II | | 8.8 | | | | |
| Polyester polyol III | | | 11.0 | | | |
| Characteristic data: | | | | | | |
| Solids content | 80 | 80 | 80 | 80 | 70 | 70 |
| Viscosity (mPa.s/25° C.) | 9000 | 18000 | 11000 | 25000 | 2000 | 32000 |

USE EXAMPLES 1 TO 3 (according to the invention) AND 4 TO 6 (Comparison Examples)

1.5% tert.-butyl perbenzoate and 1% cobalt octoate (2.2% metal content) are added to the products of Examples 1 to 6 above. These lacquers have standing times of more than 2 days. After application to steel plates, the lacquer films are heated for 40 minutes at 100° C. The dry lacquer films obtained have a thickness of approximately 50 μm.

The film properties obtained are shown in Table 3 below.

TABLE 3

|  | Use Examples | | | Comparison Examples | | |
|---|---|---|---|---|---|---|
|  | 1 | 2 | 3 | 4 | 5 | 6 |
| Pendulum hardness (sec.)[a] | 135 | 144 | 127 | 170 | 190 | 200 |
| Extensibility (mm)[b] | 5.0 | 5.5 | 5.5 | 3.0 | 1.0 | 0.4 |

TABLE 3-continued

|  | Use Examples | | | Comparison Examples | | |
| --- | --- | --- | --- | --- | --- | --- |
|  | 1 | 2 | 3 | 4 | 5 | 6 |
| Solvent resistance[c] | good | good | good | good | good | poor |

[a] The pendulum hardnesses are determined in accordance with Konig (DIN 53 157)
[b] The extensibility of the coating is determined by Erichsen indentation (DIN 53 156). An extensibility of ≦3 mm is inadequate for effective use.
[c] To determine solvent resistance, a solvent-impregnated cotton wool plug is placed on the lacquer film for 1 minute. The change in the film is then evaluated by scratching the film with a finger nail. Toluene, methoxy-propyl acetate, ethyl acetate and acetone are used as solvents.

With the exception of Comparison Example 6, the surfaces of the lacquer films are impossible or difficult to scratch.

Whereas both hard and elastic and solvent-resistant coatings are formed with the products of Examples 1 to 3 according to the invention, the products of Comparison Examples 4 to 6 show inadequate properties.

USE EXAMPLE 7 (Photochemical hardening)

65 parts by weight butyl acetate and 0.5 part by weight 2-hydroxy-2-methyl-1-phenylpropan-1-one (photoinitiator) are added to 100 parts by weight of the product of Preparation Example 1 which is then applied to a veneered chipboard in such a way that, after evaporation of the solvent, a 30 μm thick dry coating is obtained. The board is moved past beneath a Hanovia lamp (80 W/cm) at a distance of 10 cm and at a rate of 20 m/minute. A hard, elastic, scratch-resistant and water-resistant coating unaffected by chemicals is formed.

What is claimed is:

1. A process for the production of compounds containing isocyanurate groups and olefinic double bonds by reaction of components (a), (b) and (c) wherein
   (a) is a polyisocyanate component containing isocyanurate polyisocyanates which is
   (i) N,N',N''-tris-(isocyanatohexyl)-isocyanurate alone or in admixture with its higher homologs containing more than one isocyanurate ring or
   (ii) mixtures of the polyisocyanates (i) with up to 40 NCO-equivalent-%, based on the total component (a), of other polyisocyanates containing aliphatically or cycloaliphatically bound isocyanate groups;
   (b) is an olefinically unsaturated alcohol component comprising at least one hydroxyalkyl ester of acrylic acid or methacrylic acid; and
   (c) is a polyol component consisting essentially of a polyester polyol having an OH value of 80 to 350 based on (i) an acid component, of which at least 80 carboxyl equivalent-% is adipic acid, isophthalic acid or a mixture of both and (ii) a polyhydroxy component of which at least 70 hydroxyl equivalent-% is hexane-1,6-diol;
   wherein component (c) amounts to 20 to 150% by weight, based on the weight of component (b), and the reaction is carried out at with an NCO:OH equivalent ratio maintained at 0.9:1 to 1.1:1, and wherein components (b) and (c) are reacted with the polyisocyanate component in any order or in admixture.

2. A process as claimed in claim 1 wherein component (b) is 2-hydroxyethyl acrylate, 2-hydroxyethyl methacrylate, 2-hydroxypropyl acrylate, 2-hydroxypropyl methacrylate or mixtures thereof.

3. A process as claimed in claim 1 wherein component (c) is a polyester diol of adipic acid and 1,6-hexanediol.

4. A process as claimed in claim 3 wherein component (b) is 2-hydroxyethyl acrylate, 2-hydroxyethyl methacrylate, 2-hydroxypropyl acrylate, 2-hydroxypropyl methacrylate or mixtures thereof.

5. A binder for coating compositions which is hardenable by radiation or peroxides and which is the product of the process according to claim 1.

6. In an improved coating composition containing a binder hardenable by radiation or peroxides, the improvement comprises said binder being the product of the process according to claim 1.

* * * * *